US007143653B2

(12) United States Patent
Abdel-Hadi et al.

(10) Patent No.: US 7,143,653 B2
(45) Date of Patent: Dec. 5, 2006

(54) ENHANCED TRIAXIAL TESTER WITH VOLUME CHANGE DEVICE FOR MEASUREMENT OF FLOW PROPERTIES OF DRY COHESIVE PARTICULATE SYSTEMS UNDER LOW CONFINING PRESSURES

(75) Inventors: Ali Ismail Abdel-Hadi, Gainesville, FL (US); Nocolaie D. Cristescu, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 34 days.

(21) Appl. No.: 10/478,793

(22) PCT Filed: Mar. 20, 2002

(86) PCT No.: PCT/US02/08302

§ 371 (c)(1),
(2), (4) Date: Jul. 28, 2004

(87) PCT Pub. No.: WO02/075257

PCT Pub. Date: Sep. 26, 2002

(65) Prior Publication Data

US 2004/0244497 A1 Dec. 9, 2004

(51) Int. Cl.
*G01N 3/08* (2006.01)

(52) U.S. Cl. .......................... 73/819; 73/819; 73/820; 73/823; 73/825; 73/149

(58) Field of Classification Search ................. 73/819, 73/820, 823, 825, 149

See application file for complete search history.

(56) References Cited

U.S. PATENT DOCUMENTS

| 2,706,908 | A | | 4/1955 | Macroberts | |
|---|---|---|---|---|---|
| 3,166,934 | A | * | 1/1965 | Kruse et al. .................. | 73/820 |

(Continued)

FOREIGN PATENT DOCUMENTS

DE 29917940 1/2000

(Continued)

OTHER PUBLICATIONS van der Kraan, "Techniques for the Measurements of Flow Properties of Cohesive Powders", Copy Print 2000, Enschede (1996).

(Continued)

*Primary Examiner*—Hezron Williams
*Assistant Examiner*—Samir M. Shah
(74) *Attorney, Agent, or Firm*—Dennis P. Clarke; Miles & Stockbridge P.C.

(57) ABSTRACT

Disclosed is a triaxial system for testing particulate matter under substantially dry triaxial load conditions comprising: a housing means fillable with confining fluid for providing confining pressure on a sample of dry particulate matter to be tested, the housing having a channel for introduction therein and removal therefrom of the confining fluid, a load piston sealingly extends for providing a load on the sample, sample mounting means for mounting the sample within the housing, the sample mounting means including a top end platen for mounting at the top and a button end platen for disposition at the bottom of the sample, at least one flexible, impermeable membrane for enclosing the surface of the sample other than its ends, fluid passage means connecting the housing to a volume change sensor for freely delivering confining fluid thereto, and a volume change sensor adapted to measure the volume of confining fluid delivered thereto through the fluid passage means. Also disclosed is a test method for employing the above system to test particulate matter.

8 Claims, 9 Drawing Sheets

New setup for performing triaxial tests under very low confining pressures and a new method for volume change measurement.

U.S. PATENT DOCUMENTS

| | | | |
|---|---|---|---|
| 3,535,922 A | 10/1970 | Pocock | |
| 3,608,367 A | 9/1971 | Karol | |
| 3,616,685 A * | 11/1971 | Strom | 73/84 |
| 3,635,078 A | 1/1972 | Wissa | |
| 3,820,385 A | 6/1974 | Cordoba | |
| 3,975,950 A | 8/1976 | Erdei | |
| 4,502,338 A * | 3/1985 | Smith et al. | 73/819 |
| 4,579,003 A | 4/1986 | Riley | |
| 4,672,842 A * | 6/1987 | Hasselmann | 73/49.2 |
| 4,679,441 A | 7/1987 | Johnson et al. | |
| 4,697,457 A | 10/1987 | Fochtman et al. | |
| 4,715,212 A | 12/1987 | Johanson | |
| 4,811,601 A * | 3/1989 | Tolan | 73/290 B |
| 4,854,175 A | 8/1989 | Budhu | |
| 4,885,941 A | 12/1989 | Vardoulakis et al. | |
| 5,025,668 A | 6/1991 | Sarda et al. | |
| 5,159,828 A | 11/1992 | Steiger et al. | |
| 5,226,310 A | 7/1993 | Steiger | |
| 5,265,461 A | 11/1993 | Steiger et al. | |
| 5,323,655 A * | 6/1994 | Eagan et al. | 73/432.1 |
| 5,435,187 A | 7/1995 | Ewy et al. | |
| 6,003,382 A | 12/1999 | Puri et al. | |
| 6,247,358 B1 | 6/2001 | dos Santos | |
| 6,615,638 B1 * | 9/2003 | Lochner et al. | 733/1.74 |

FOREIGN PATENT DOCUMENTS

DE          29917940 U1 *   1/2000

OTHER PUBLICATIONS

Schwedes, "Testers for Measuring Flow Properties of Particulate Solids", Proceedings Reliable Flow of Particulate Solids III, P[orsagunn, Norway, pp. 3-40 (Aug., 1999)].

Cazacu, et al., "A New Constitutive Model for Alumina Powder Compaction", 103-112, No. 15.

Cristescu, "Recent Developments on Computer Modeling of Powder Metallurgy Operations," keynote lecture at NATO Advanced Research Workshop, May 15-18, 2000 Kiev, Ukraine.

Cristescu, et al., "Constitutive equation for compaction of ceramic powders", IUTAM Symposium on Mechanics of Granular and Porous materials, Kluwer Academic Publishers, 117-128, (1997).

Jin et al., "A Constitutive Model for Powder Materials", Journal of Engineering Materials and Technology, 1-8, vol. 120 (1998).

Bishop and Henkel, "The Measurement of Soil Properties in the Triaxial Test", Edward Arnold LTD, London (1957).

* cited by examiner

Fig. 1 New setup for performing triaxial tests under very low confining pressures and a new method for volume change measurement.

Fig. 2 New setup for performing triaxial tests under moderate confining pressures and a new method for volume change measurement.

Fig. 3 Details of the electronic volume change sensor suitable for ultra low, low and moderate confining pressures currently designed for up to 414KPa (60psi).

Fig. 4 Stress-strain curves in deviatoric test for dry alumina for four initial densities shown and confining pressure of 9.7KPa (1.4psi). A structural instability is exhibited at a certain stress level and for certain initial densities.

Fig. 5 Stress-volumetric strain curves in deviatoric test for dry alumina, left side of Fig. 4 enlarged.

Fig. 6 Stress-strain curves in deviatoric test for dry alumina for four initial densities shown and confining pressure of 16KPa (2.32psi). Similar structural instability is exhibited at a certain stress level and for certain initial densities, is shown enlarged.

Fig. 7 Stress-volumetric strain curves in deviatoric test for dry alumina, same as left side of Fig. 6 enlarged.

Fig. 8 Mean stress-volumetric strain curves for microcrystalline cellulose obtained in a hydrostatic test with small unloading following a short period of creep at 68.95Kpa (10psi).

Fig. 9 Bulk modulus-mean stress curves for microcrystalline cellulose obtained in the hydrostatic test in Fig. 8 at 68.95Kpa (10psi).

Fig. 10 Stress-strain curves for unloading and reloading for microcrystalline cellulose following a short term creep of ten minutes, to determine the static elastic constants, at a confining pressure of 68.95Kpa (10psi).

Fig. 11 Bulk moduli-stress curves for microcrystalline cellulose obtained in the hydrostatic test of Fig. 8 and the deviatoric test of Fig. 10 at 68.95Kpa (10psi).

Fig. 12 Mean stress-volumetric strain curves for microcrystalline cellulose obtained in a hydrostatic test with small unloading following a short period of creep up to 344.74Kpa (50psi).

Fig. 13 Bulk moduli-mean stress curves for microcrystalline cellulose obtained in the hydrostatic test in Fig. 12 up to 344.74Kpa (50psi).

Fig. 14 Stress-strain curves for unloading and reloading for microcrystalline cellulose following a short term creep of ten minutes, to determine the static elastic constants, at a confining pressure of 344.74Kpa (50psi).

Fig. 15 Bulk moduli-stress curves for microcrystalline cellulose obtained in the hydrostatic test of Fig. 12 and the deviatoric test of Fig. 14 at 344.74Kpa (50psi).

ENHANCED TRIAXIAL TESTER WITH VOLUME CHANGE DEVICE FOR MEASUREMENT OF FLOW PROPERTIES OF DRY COHESIVE PARTICULATE SYSTEMS UNDER LOW CONFINING PRESSURES

CROSS-REFERENCE TO RELATED APPLICATIONS

This application claims priority based on PCT Application No. PCT/US02/08302 filed 20 Mar. 2002.

BACKGROUND OF THE INVENTION

1. Field of the Invention:

The inventive concept relates to the field of measurement of volume changes in dry particulate systems in triaxial testers.

2. Description of the Prior Art

It is not an exaggeration to say that particles impact every aspect of our modern lives. They are found in our food, aerosols, cements, cosmetic preparations, drug preparations, dyes etc. All industries deal with particles at one point or another; examples being chemical, pharmaceutical, food and mining, to name a few. The importance of particle chemistry and behavior cannot be overstressed. In the past 30 years, the measurement of flow properties of particulate systems has received considerable interest in powder technology. The study of powder flow has evolved into the new field of powder mechanics; however, this field is still in its infancy due to the complex nature of powder flow. The present invention focuses on one of the tools that is available to study powder flow, namely, an enhanced triaxial tester.

Following is a brief comparative survey of conventional flow testers, their classification, and several techniques for the determination of volume change.

There are many different kinds of flow testers that are commercially available, which allow the determination of some measure of flowability. Examples are, but not limited to, Jenike's shear cell, annular shear cells, Hosokawa tester, Johanson Indicizers, and uniaxial tester. There are a few other flow testers that are used for research purposes and are owned by a handful of research institutions worldwide, such as the biaxial tester, and true triaxial tester. These testers are extremely complicated to build and to operate and they haven't been developed to a stage of practical utility. A true triaxial tester can cost over half a million dollars. Many of the commercially available devices are very empirical in nature and the flow parameters obtained are based on assumptions that do not have a solid scientific foundation. Moreover, they don't provide enough information for the formulation of a general 3-dimensional constitutive model. In addition most of these devices test powder already in flow or no-flow but are unable to determine the conditions when the powder is partially in flow and partially in no-flow. An extensive review of these testers can be found in van der Kraan, ["*Techniques for the Measurement of Flow properties of Cohesive Powders*", Copy Print 2000, Enschede (1996)] and Schwedes, ["*Testers for measuring Flow Properties of particulate Solids*", Proceedings Reliable Flow of Particulate Solids III, P{orsagrunn, Norway, pp. 3–40 (August, 1999)]. See also, Cazacu, et al, "A New Constitutive Modelfor Alumina Powder Compaction," 103–112, No. 15; Cristescu, "Recent Developments on Computer Modeling of Powder Metallurgy Operations," keynote lecture at NATO Advanced Research Workshop, May 15–18, 2000 Kiev, Ukraine; Cristescu, et al, "Constitutive equation for compaction of ceramic powders," IUTAM Symposium on Mechanics of Granular and Porous materials, 117–128, (1997) Kluwer Academic Publishers, and Jin, et al, "A Constitutive Model for Powder Materials," Journal of Engineering Materials and Technology. 1–8, vol. 120 (1998).

The triaxial tester is another tester that could be potentially useful as a powder flow tester, however in its currently available form it is not suitable for the study of dry cohesive powders. The present invention is concerned with an enhancement of the triaxial cell, which is an indirect shear tester. The classical triaxial cell (FIG. 1) was invented about a century ago for the purpose of characterizing soil behavior over a range of pressures that is of interest in civil engineering and mining applications. See, e.g., U.S. Pat. No. 4,502,338. Most of the triaxial shear testing equipment uses the specimen in a wetted or saturated form; however, this might interfere with, or change the inherent properties of the powder. In addition they are primarily designed to operate under elevated pressures that are applicable to geomechanics. This motivated the development of the dry system and the volume change device applicable to low confining pressures.

The testers fall into two main categories, i.e., direct and indirect shear testers. In direct shear testers the location of the shear zone or shear plane is determined by the design of the tester, whereas in indirect shear testers the powder develops its own shear plane or shear zone before failure due to its state of stress.

There are three principal methods that can be used to measure volume change [see Bishop and Henkel, "*The Measurement of Soil Properties in the Triaxial Test*", Edward Arnold LTD, London (1957)]: (a) by measuring the volume of fluid entering the cell (when the specimen is compressing) or leaving the cell (when the specimen is dilating), (b) by measuring the volume of fluid entering or leaving the interstitial space (or pore space) of the soil, (c) by the direct measurement of the change in length and diameter of the specimen. Methods (b) and (c) are not applicable to dry powders. Method (b) is not applicable because the sample is dry, therefore no fluid can be introduced, and moreover air, being compressible, is not a good candidate for volume measurements. Method (c) is highly inaccurate at very low confining pressures because the pressure exerted by the mechanical device on the specimen for measuring the diameter change is of the same order of magnitude as the confining pressure.

There are several devices available for measuring volume change under pressure. The first one is a self-compensating U-tube in which mercury is used to provide pressure. A spring is attached to one side of the U-tube to compensate for the head resulting from the displacement of the mercury. The accuracy of such devices is about 0.01% of the initial volume of the sample, i.e., about 0.06 cm$^3$. If regulated air supply is available, the direct burette or bellows techniques can be alternatively considered. In the direct burette technique, connections are made from the cell to the burette, which is partially filled with fluid and confining air pressure is directly applied to the top of the fluid. The accuracy of this method is about 0.05 cm$^3$. All of the above methods require manual operation and are not suitable for automation or on-line monitoring of the volume change. There is an enhanced version of the direct burette method which utilizes a float, placed on top of the fluid in the burette, with a rod that forms a push rod of an LVDT (linear variable differential transducer) for computerized data acquisition. The bellows based technique uses bellows as the name suggests which is connected to an LVDT. The bellows expand and contract proportionally to the volume change and the LVDT provides the input data for automation. The accuracy of the new volume change device is about 0.005% of the initial volume, which translates to about 0.009 cm$^3$. The accuracy of the volume measurements is about an order of magnitude better than that of currently existing devices.

As one focuses on smaller particle sizes at the micro level, or as confining loads decrease, the influence of interparticle cohesive forces increases. The potential for significant volume change upon shearing can be much greater for particles with significant cohesion since such particles can form loose networks of contacts which can move as rigid bodies and cause dilation of the bulk material or, can collapse to denser configurations. These volume changes can be quite large and can occur at very short periods of time. As a result, the conventional volume change devices described above are unable to capture such events. Thus, there is a critical need for developing techniques that are suitable for characterizing such systems. A few researchers have developed equipment capable of measuring the biaxial and triaxial response of dry samples. Van der Kraan, supra, describes a technique for measuring the volume change of dry powder systems. Using this technique, a series of triaxial compression tests on alumina powder (mean particle size 100 gm) have been carried out under a confining pressure of 9.7 KPa (1.4 psi) and 16 KPa (2.3 psi) respectively using a conventional triaxial compression cell. A set of hydrostatic tests followed by triaxial compression tests was done on microcrystalline cellulose (mean particle size 20 gm). The main features of the behavior have been captured with improved accuracy. The equipment enhancements represent technological advances that allow more accurate measurements over a wider range of stresses and strains and volumetric deformations that can be explored utilizing other prior art systems and techniques.

None of the powder flow testers presently available are equipped with a device capable of automatic volume change sensing. Moreover, the operating principles on which these devices rely inhibit the use of any volumetric change device. Examples of commercially available systems are the Johanson Indicizer described in U.S. Pat. No. 4,715,212 and the computer control shear cell tester described in U.S. Pat. No. 6,003,382, both of which are examples of the direct shear testers discussed above. Other typical prior art triaxial testers are described in U.S. Pat. Nos. 4,679,441; 5,265,461; 5,435,187; 6,247,358; 4,579,003; 5,025,668 and 5,159,828. The entire contents and disclosures of all U.S. patents named herein are incorporated herein by reference.

Some of the triaxial testing devices employed by civil engineers are equipped with a volume change device; however, these volume change devices have been designed to operate without significant errors at elevated pressures which are encountered in geomechanics. None of these devices are applicable to measure volume change in dry particulate systems at low confining pressures.

SUMMARY OF THE INVENTION

A new technique has been developed to measure volume change of dry particulate systems at very low confining pressures, typical in storage and transport of particulate systems. It is fully automated, very responsive, has no moving parts, uses no toxic fluids and is ideally suited for developing constitutive models.

One embodiment of the invention relates to a triaxial system for testing particulate matter under substantially dry triaxial load conditions comprising:

a housing means fillable with confining fluid for providing confining pressure on a sample of dry particulate matter to be tested, the sample having a top and a bottom, the housing having a channel for introduction therein and removal therefrom of the confining fluid, the housing having an opening therein through which a portion of a load piston sealingly extends for providing a load on the sample, sample mounting means for mounting the sample within the housing, the sample mounting means including a top end platen for mounting at the top and a bottom end platen for disposition at the bottom of the sample, at least one flexible, impermeable membrane for enclosing the surface of the sample other than its ends and preventing the confining fluid from directly contacting the sample and preventing sample from being expelled from the portion of the sample covered by the membrane, fluid passage means connecting the housing to a volume change sensor for freely delivering confining fluid thereto, and a volume change sensor adapted to measure the volume of confining fluid delivered thereto through the fluid passage means.

A second embodiment of the invention concerns a test method for triaxially testing a sample comprising dry particulate material under dry triaxial load conditions comprising providing:

a housing means fillable with confining fluid for providing confining pressure on the sample of dry particulate matter to be tested, the sample having a top and a bottom, the housing having a channel for introduction therein and removal therefrom of the confining fluid, the housing having an opening therethrough through which a portion of a load piston sealingly extends for providing a load on the sample, sample mounting means for mounting the sample within the housing, the sample mounting means including a top end platen for mounting at the top and a bottom end platen for disposition at the bottom of the sample, at least one flexible impermeable membrane for enclosing the surface of the sample other than its ends and preventing the confining fluid from directly contacting the sample and preventing sample from being expelled from the portion of the sample covered by the membrane, fluid passage means connecting the housing to a volume change sensor for freely passing confining fluid therethrough, the test method comprising:

placing the sample in the sample mounting means, loading the sample by introducing a confining fluid under pressure into the housing to provide a constant confining pressure on the sample, allowing the sample's pore pressure to equilibrate with the pressure of the confining fluid, applying a load piston to the top end platen to apply a known load on the sample, the piston sealingly extending through the confinement vessel to contact the sample, and measuring and recording the volume of confining fluid displaced through the fluid passage means connecting the housing to the volume change sensor during the test.

The system is particularly suited for the low confining stress levels experienced in typical storage devices or in rapid shearing flow measurements as particulate systems transition from frictional to fluid-like flow. The system comprises five major components: 1) a triaxial cell, 2) an integrated pressure sensor module, 3) a volume change sensor, 4) a data acquisition system, and 5) a low-pressure line.

The volume measurement method of the invention eliminates the need for cumbersome pressure lines and an additional volume change device. The confining pressure is applied with, e.g., a water head and the volume change is measured using the electronic scale, utilizing the same water head that provided the initial pressure. The system of the invention improves the accuracy, reliability, and repeatability of the measurements and minimizes human error. Further, the system allows the measurement of volume changes for dry powders as well as the study of flow/no flow conditions for any stress state and the obtention of all parameters for a three dimensional tensorial model. In addition, the system of the invention permits the testing of the sensitivity of the sample cohesiveness to humidity and pressure. Finally, the system allows separate fluid flow into or out of the sample such that the effect of humidity and the absorption of fluids and/or permeability can be studied at various loading and deformation conditions.

DETAILED DESCRIPTION OF THE INVENTION

Figure 1:
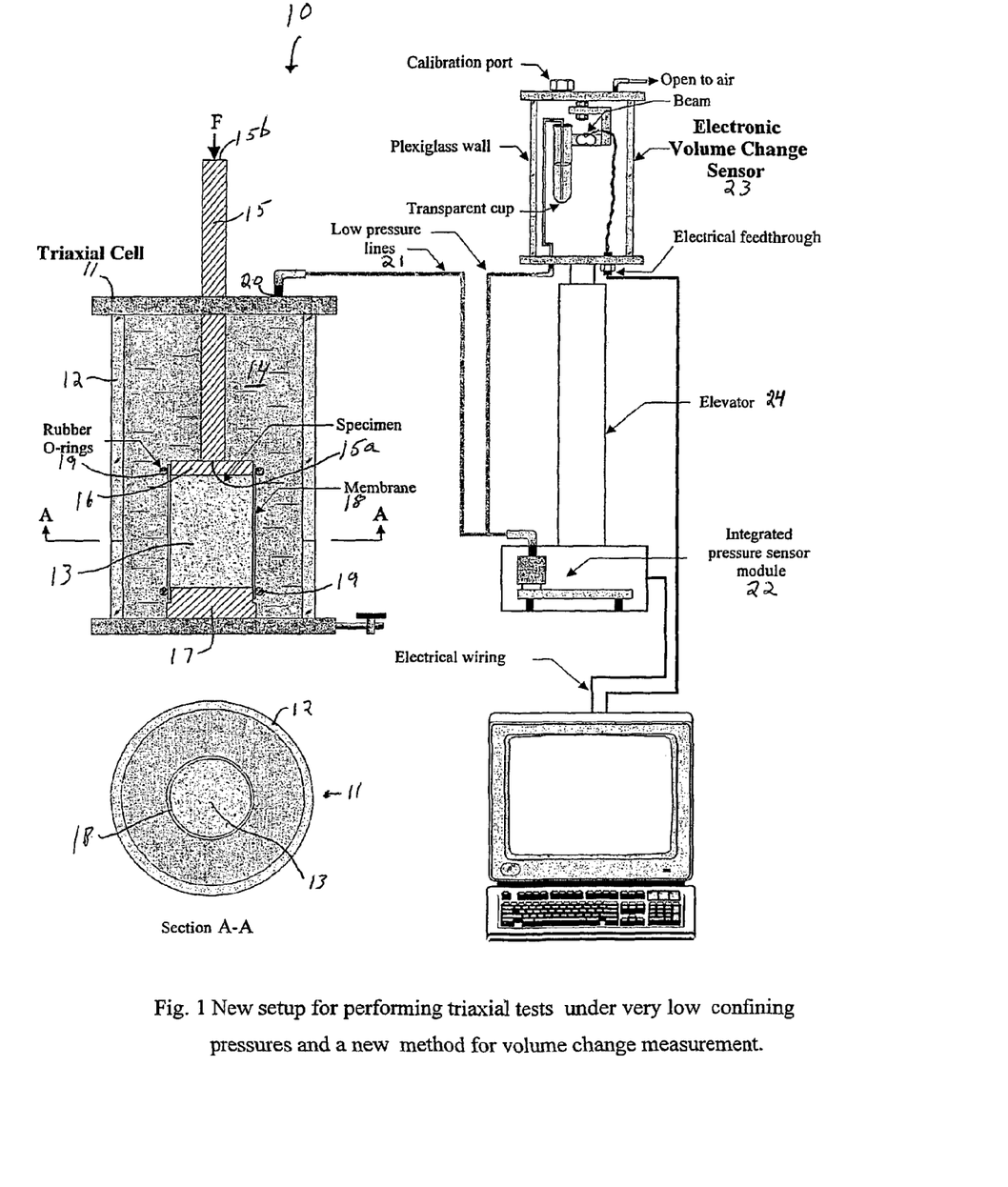
FIG. 1 depicts a typical, conventional triaxial cell and an embodiment of the present invention for performing triaxial tests under very low confining pressures and a new method for volume change measurement.

The system of the present invention includes a computer controlled triaxial cell, low pressure lines, an integrated pressure sensor module, and volume change electronic sensor as depicted in FIG. 1. The confining pressure is applied with, e.g., a water head and the volume change is measured with a novel electronic sensor. The method and system of the invention eliminate the need for cumbersome pressure lines and a complex volume change device that might inherently change the volumetric response of the material under small confining pressures, by sharing some of the pressure for its operation.

The aim of this technique is to obtain more accurate information on the deformation, failure and flow behavior of cohesive powders under a variety of loading conditions and deformation rates. The technique allows covering the entire pressure regime that is covered by commercially available and industrially applied powder flow testers. It bridges the gap of multiple devices, whose ranges of test conditions do not overlap, thus facilitating cross-calibration of equipment and the increased confidence (and reliability) of all compaction data obtained. The investigation of the effect of initial porosity on powder flowability and the determination of the elastic moduli of a particulate system were chosen to test the new experimental setup.

Referring to the Drawings:

FIG. 1 shows a longitudinal sectional view of a preferred triaxial test system of the present invention hereinafter referred to as test system 10. The triaxial test cell 11 includes a housing 12 that it should be understood consists of a number of sections that are joined and maintained together, by conventional fasteners. For convenience, the different sections and their connection arrangement have not been shown nor has an arrangement for providing access into a sample vessel 13 that, it should be understood, is included within the test cell. While not specifically shown, the test cell 11, it should be understood, includes various compartments arranged therein that can be taken apart so as to allow access to the vessel 13 to position therein a specimen of a particulate material that is to be subjected to triaxial or deviatoric axial stress loading.

The interior of the test cell 11 is provided to contain a confining fluid 14 that can be conveniently drained to provide access therein as by opening fasteners, not shown, and appropriately breaking apart the test cell housing 11 for positioning and removal of test specimen from vessel 13. Vessel 11 is open to a cylindrical opening (not shown) of an upper portion of housing 12. The test specimen holding vessel 13 is to be positioned opposite to the opening in the upper portion of the housing, and a loading piston 15 is arranged to travel sealingly within that cylindrical opening, a face 15a thereof moving into test cell 11 against an upper platen 16 of test specimen vessel 13.

The test specimen vessel 13 comprises the upper platen 16, lower platen 17 and a preferably cylindrical, flexible membrane 18 which is impermeable to the confining fluid 14 as well as any fluid that might be contained within the test sample. The membrane 18 completely surrounds at least portions of the outer faces of the upper and lower platens 16 and 17 (both also preferably cylindrical in shape), and are sealingly engaged thereagainst by O-rings 19 (although it will be understood by those skilled in the art that any conventional sealing device may be employed for this purpose, provided that it is sufficient to maintain a sufficiently strong seal against the upper and lower platens to prevent leakage of fluid into or out of test specimen vessel 13).

FIG. 1 shows a loading force, as arrow F, being applied against piston face 15b to urge the piston opposite end into the vessel 11 of test cell housing 12. In such operation the housing is generally held stationary as the loading force is applied to piston 15. The force F applied by piston 15 against the upper platen 16 exerts a compressive force against the test specimen in vessel 13 (which is preferably fully loaded with test sample) which distorts the flexible membrane 18, thereby exerting an interior, expansive force against the confining fluid 14. An opening 20 is provided in housing 12 for low pressure fluid transfer line 21 which allows confining fluid 14 displaced by the expansive force described above to pass to the integrated pressure sensor and control device 22 and volume change sensor 23. Pressure control device 22 is shown connected through line 21 into the test cell vessel 11 for controlling the confining pressure. Elevator 24 is provided to raise and lower the volume charge sensor to increase or decrease the pressure on the confining fluid.

Figure 2:
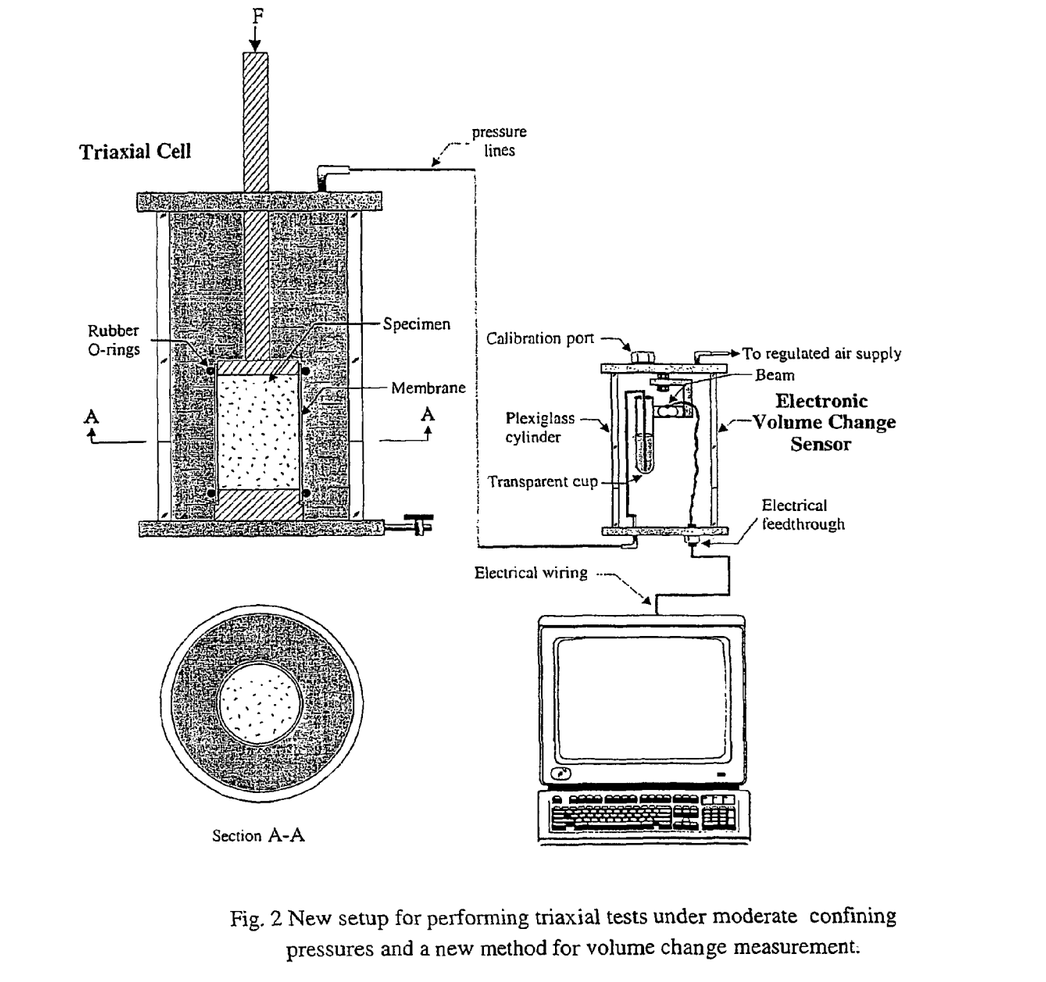
FIG. 2 depicts an embodiment of the invention for moderate confining pressures and a new method for volume change measurement.

FIG. 2 shows a system substantially identical to that of FIG. 1 except that the pressure sensor and elevator are omitted.

Figure 3:
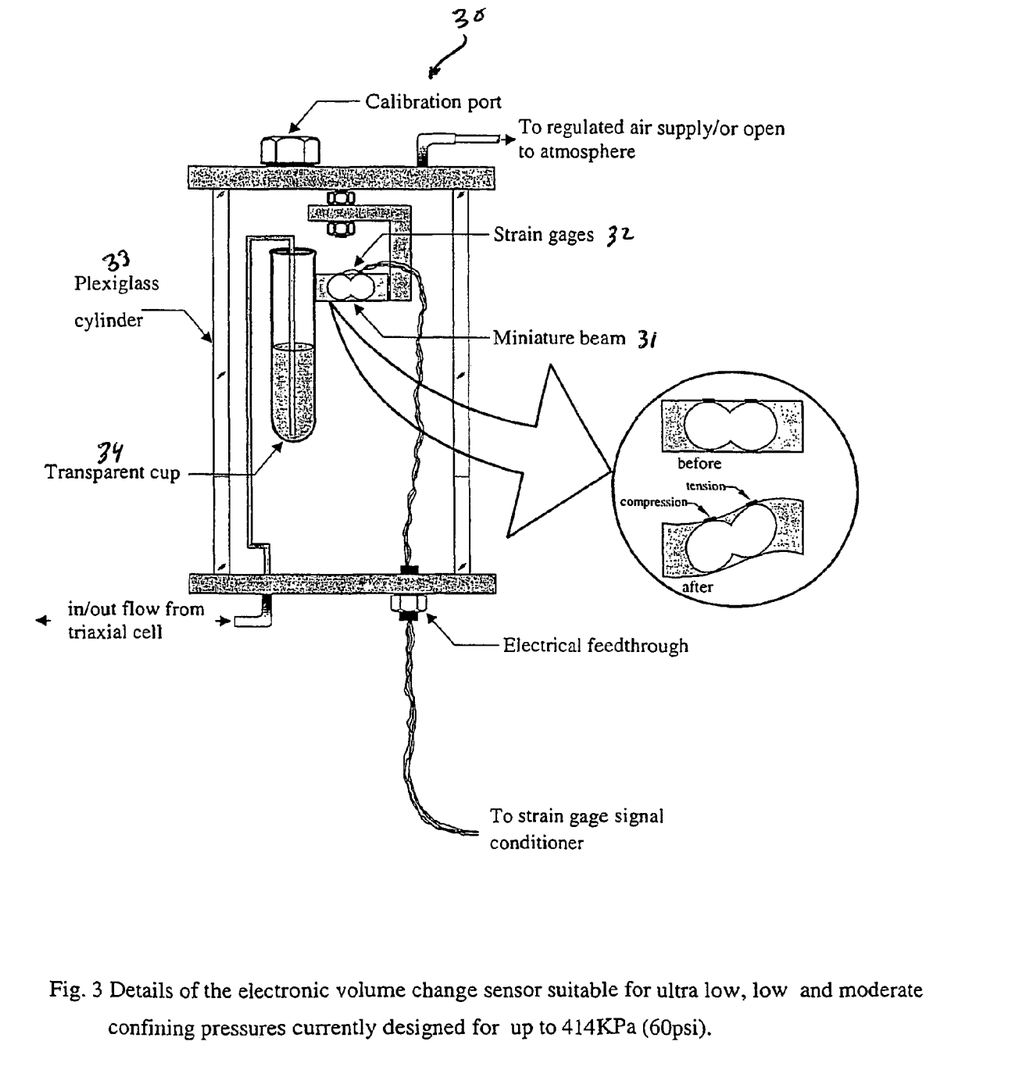
FIG. 3 depicts details of the electronic volume change sensor suitable for ultra low, low and moderate confining pressures designed for up to about 414 KPa (60 psi).
Figure 4:
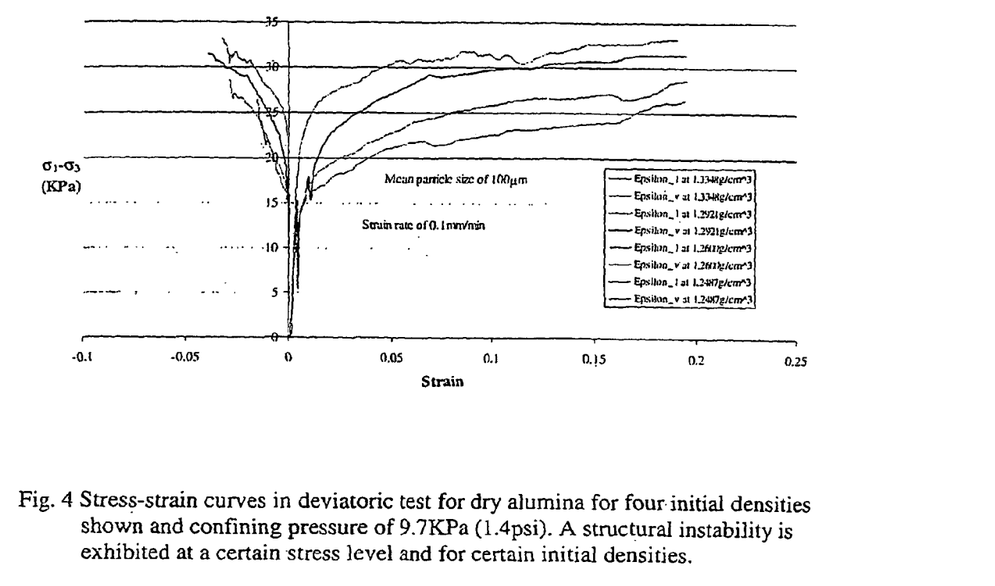
FIG. 4 sets forth stress-strain curves in deviatoric test for dry alumina for four initial density. shown and confining pressure of 9.7 KPa (1.4 psi).
Figure 5:
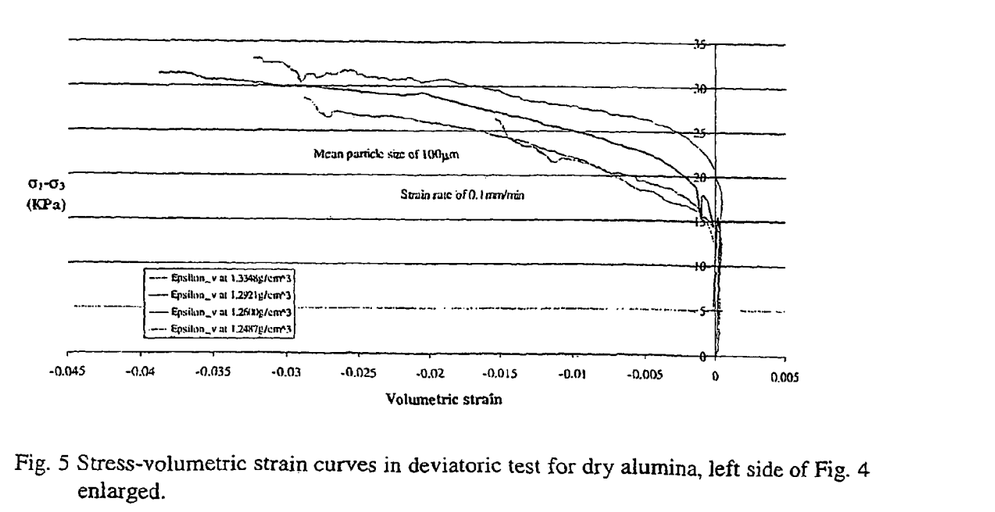
FIG. 5 sets forth stress-volumetric strain curves in deviatoric test for dry alumina (left side of FIG. 4 enlarged).
Figure 6:
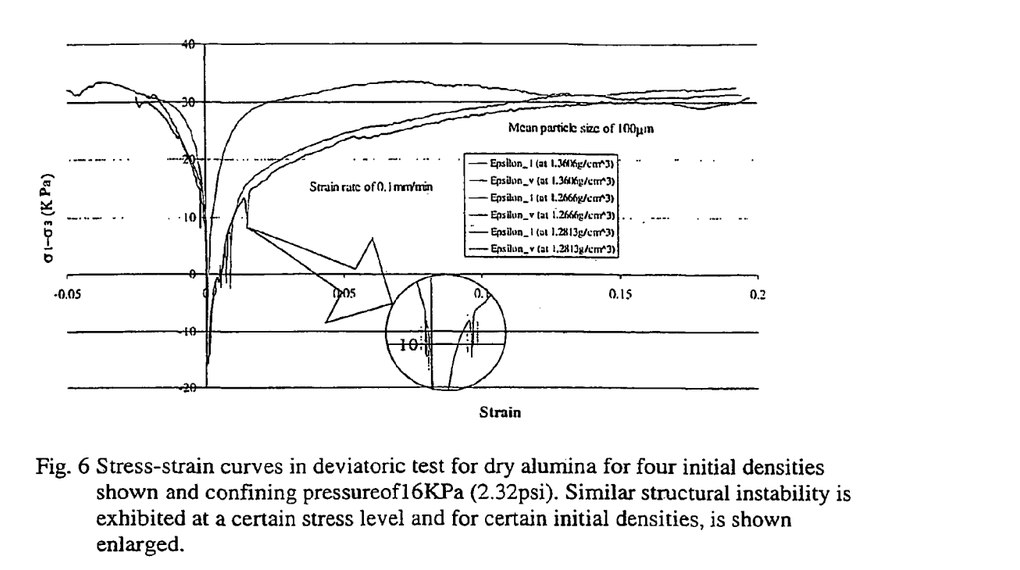
FIG. 6 sets forth stress-strain curves in deviatoric test for dry alumina for four initial densities shown and confining pressure of 16 KPa (2.32 psi). Structural instability is exhibited at a certain stress level and for certain initial densities (shown enlarged).
Figure 7:
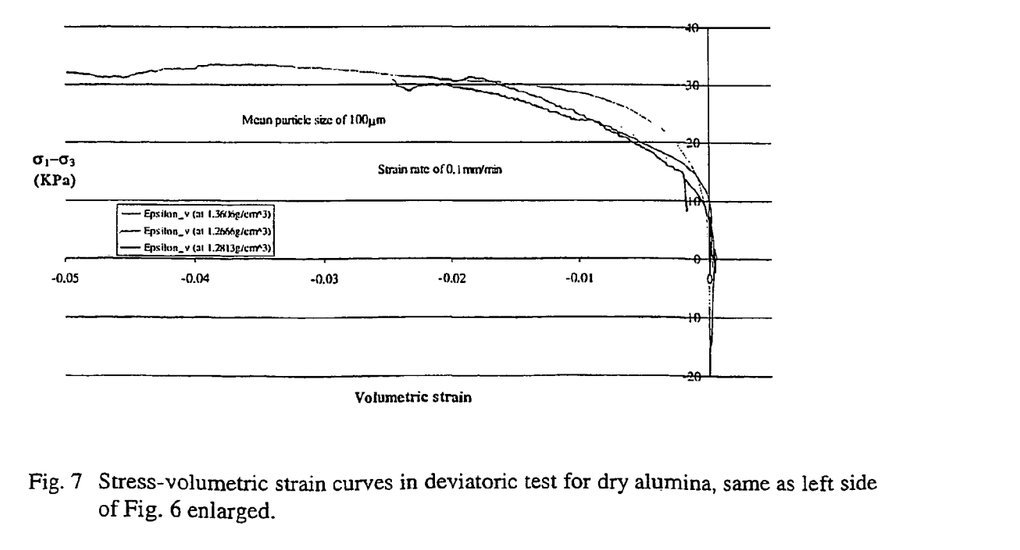
FIG. 7 sets forth stress-volumetric strain curves in deviatoric test for dry alumina (left side of FIG. 6 enlarged.
Figure 8:
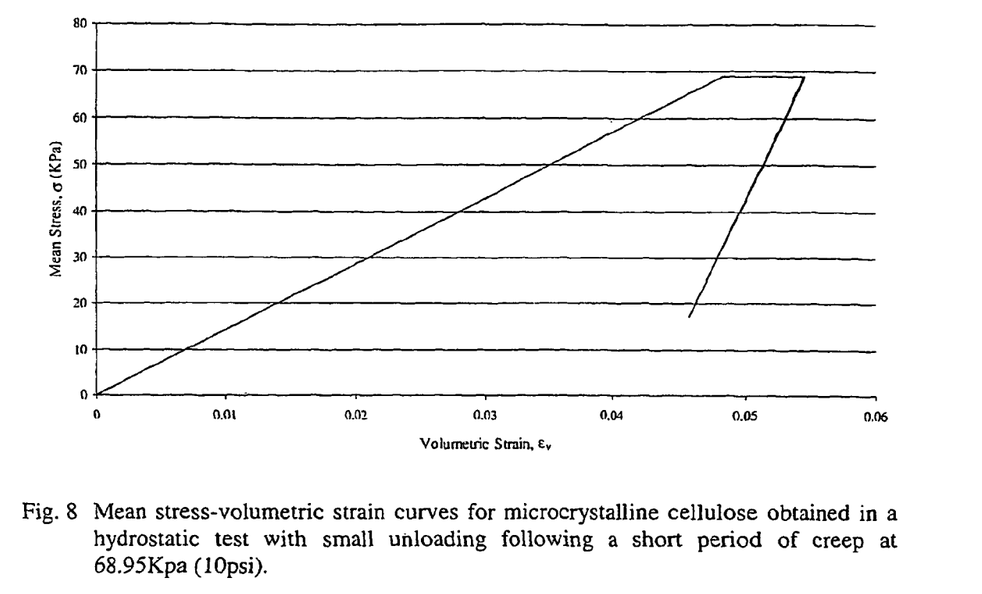
FIG. 8 sets forth mean stress-volumetric strain curves for microcrystalline cellulose obtained in a hydrostatic test with small unloading following a short period of creep at 68.95 Kpa (10 psi).
Figure 9:
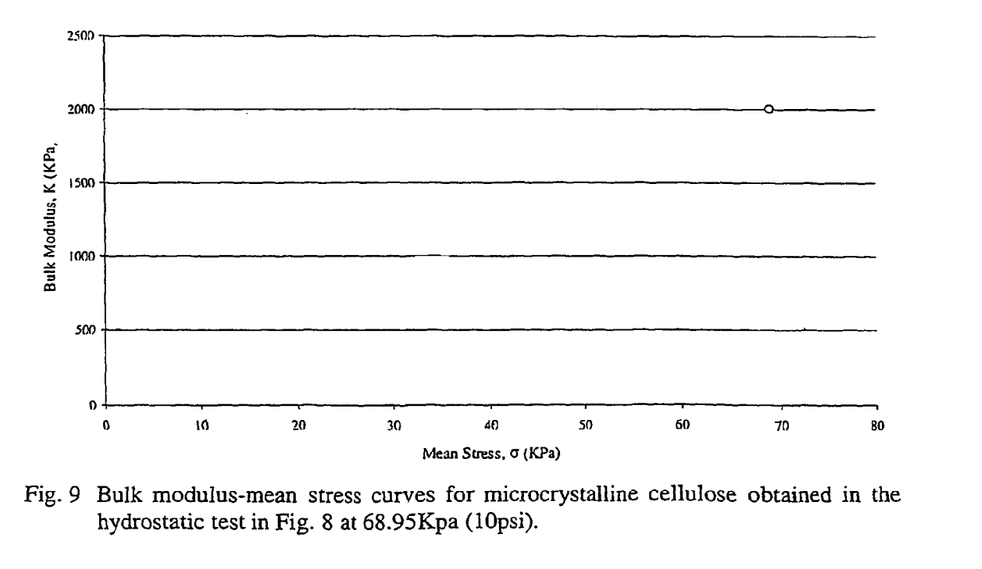
FIG. 9 sets forth bulk modulus-mean stress curves for microcrystalline cellulose obtained in the hydrostatic test in FIG. 8 at 68.95 Kpa (10 psi).
Figure 10:
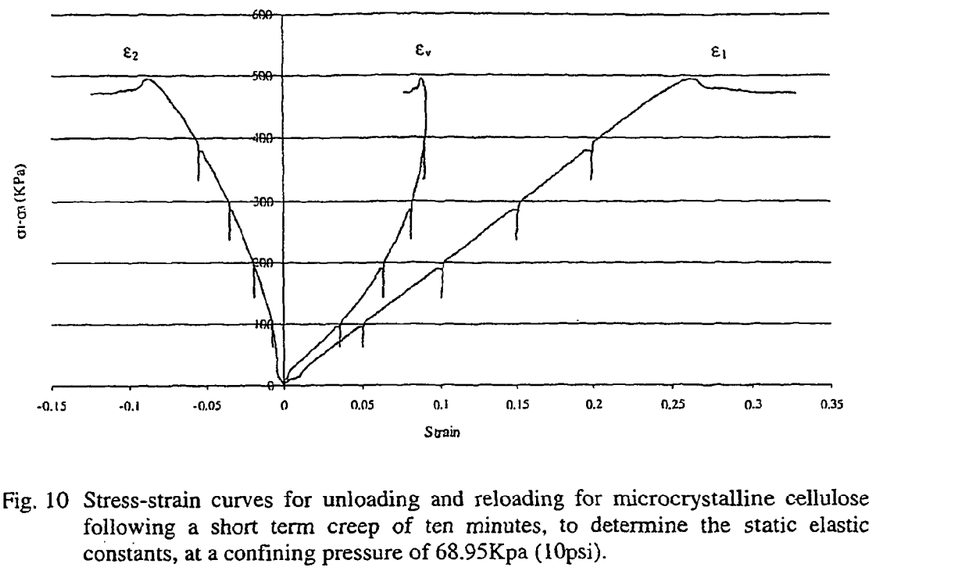
FIG. 10 sets forth stress-strain curves for unloading and reloading for microcrystalline cellulose following a short term creep of ten minutes, to determine the static elastic constants, at a confining pressure of 68.95 Kpa (10 psi).
Figure 11:
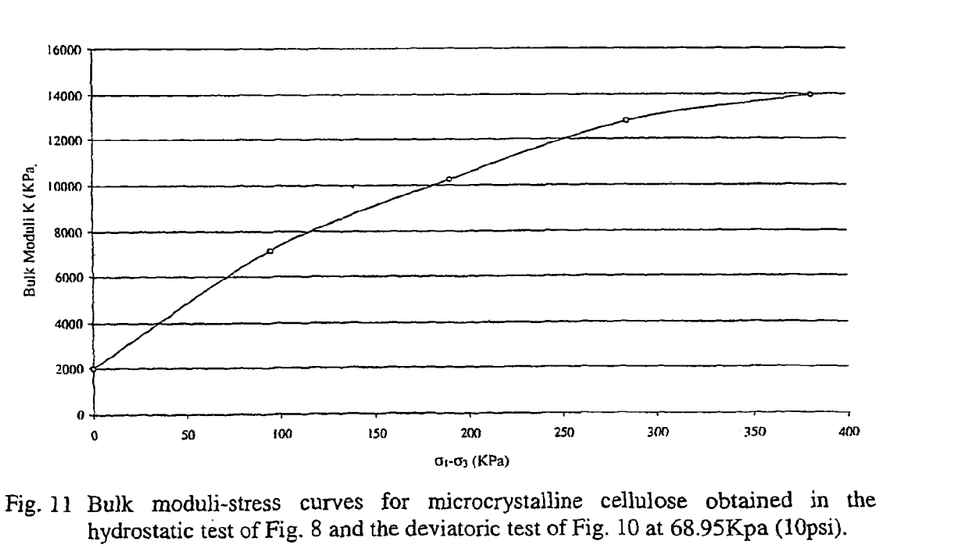
FIG. 11 sets forth bulk moduli-stress curves for microcrystalline cellulose obtained in the hydrostatic test of FIG. 8 and the deviatoric test of FIG. 10 at 68.95 Kpa (10 psi).
Figure 12:
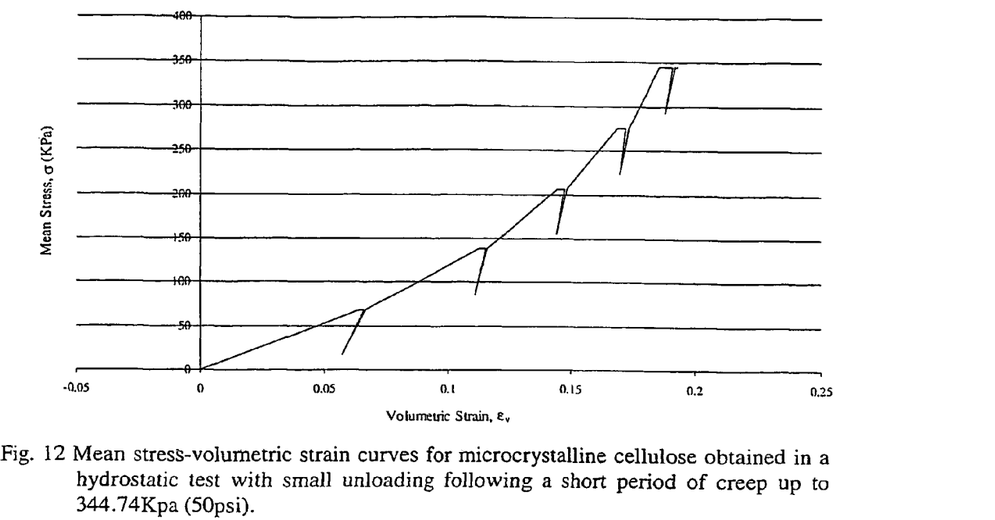
FIG. 12 sets forth mean stress-volumetric strain curves for microcrystalline cellulose obtained in a hydrostatic test with small unloading following a short period of creep up to 344.74 Kpa (50 psi).
Figure 13:
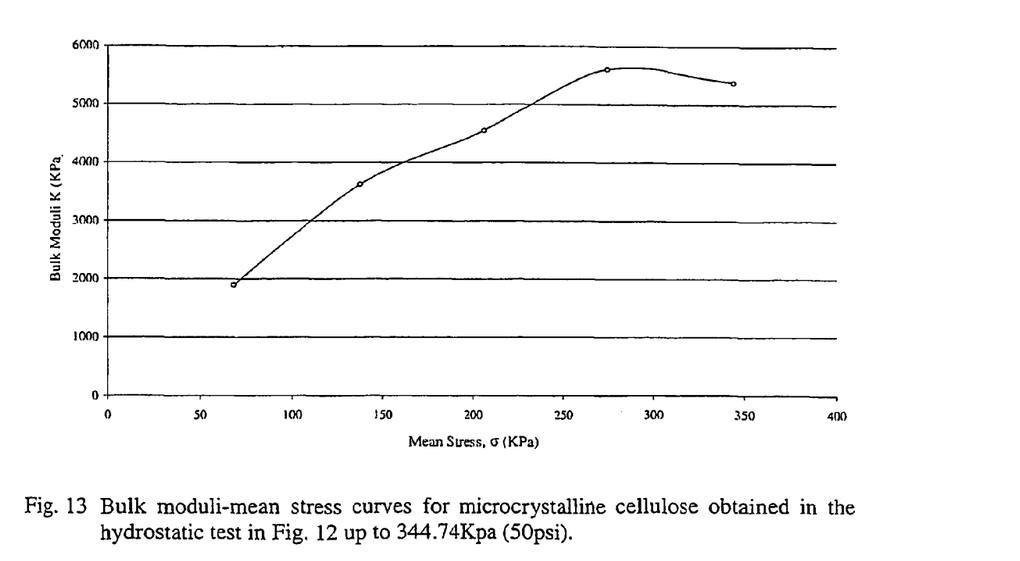
FIG. 13 sets forth bulk moduli-mean stress curves for microcrystalline cellulose obtained in the hydrostatic test in FIG. 12 up to 344.74 Kpa (50 psi).
Figure 14:
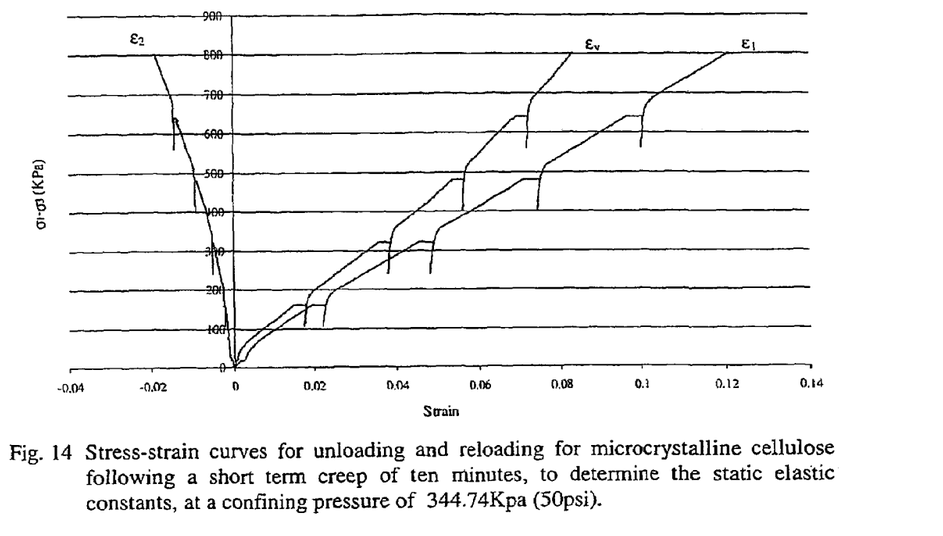
FIG. 14 sets forth stress-strain curves for unloading and reloading for microcrystalline cellulose following a short term creep of ten minutes, to determine the static elastic constants, at a confining pressure of 344.74 Kpa (50 psi).
Figure 15:
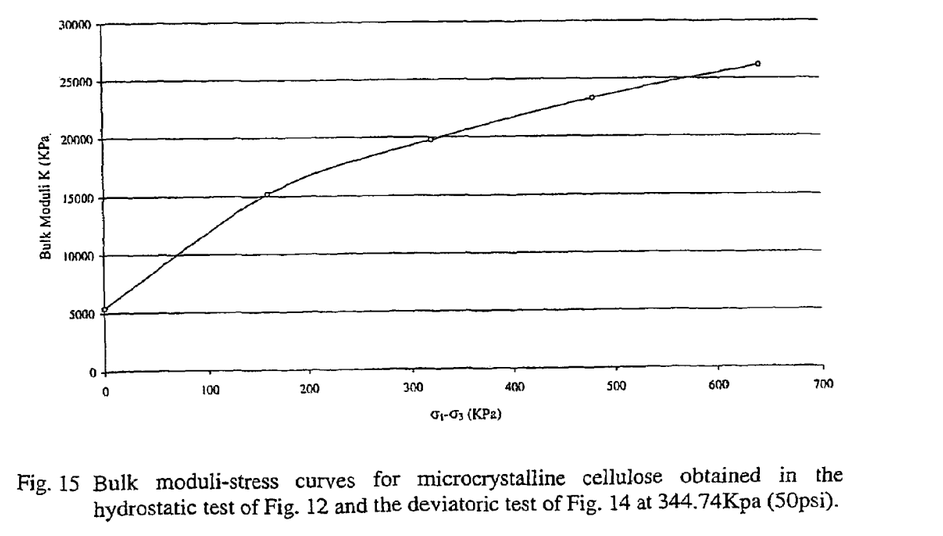
FIG. 15 sets forth bulk moduli-stress curves for microcrystalline cellulose obtained in the hydrostatic test of FIG. 12 and the deviatoric test of FIG. 14 at 344.74 Kpa (50 psi).

One embodiment of the volume change device is shown in FIG. 3, essentially comprises a tiny beam 31 containing strain gages 32 houred in houring 33 that deflects linearly as load is applied to it. One end of the beam is supported rigidly and the other end of the beam is free to deflect. A light transparent cup 34 is rigidly fitted to the beam. The cup is partially filled with water (confining fluid) to avoid any air from re-entering the system. The beam has two arms that prevent any rotation of the cup, i.e. it is allowed to move up and down but it remains vertical. The beam after deflection is shown in FIG. 3 (magnified and exaggerated for clarity). This is accomplished, according to the present invention, in a novel and ingenious manner without the introduction of any moving parts. The beam is created, e.g., from a single rectangular aluminum block; the internal part of the block having been machined away in such a way as to vary the flexural rigidity in a predetermined fashion. The center of the arms and the two ends are made the most rigid, while the two tiny sections on each arm are, preferably, the least rigid. The entire assembly is shown in FIG. 3. Four extra sensitive strain gages are fitted to the beam, two in tension and two in compression where the longitudinal strains are usually designed to be maximum, i.e. at the two weakest points. A full bridge configuration is also preferably used for the strain gages, which has a circuit sensitivity four times that of a single strain gage. In addition, the bridge arrangement is, preferably, temperature compensated. Thus it is not affected by ambient temperature changes. Furthermore the strain gages are, preferably, cross-connected so that the beam is not sensitive to changes in torsion.

The present invention is predicated on the development and utilization of enhanced triaxial test equipment in which a cylindrical specimen is subjected to lateral pressure and to an axial force. In successive tests, the lateral pressure is steadily increased. In each test the axial force is increased up to failure. The axial strain is recorded by the variation of the distance between platens, while the volumetric strain is measured by the variation of the volume of fluid surrounding the specimen. A typical experimental setup for low confining pressures is shown in FIG. 1 and a similar setup with the volume change sensor pressurized for higher confining pressures is shown in FIG. 2. The accuracy and reliability of the method was tested and compared to a traditional volume change device and it was implemented for the assessment of behavior of particulate systems using triaxial testing under very low confining pressures. In addition, because the configuration allows the confining pressure to be independent of the pressure (and gas) in the interstitial space (or pore space) inside the sample, one can test the sensitivity of the sample cohesiveness to humidity and pressure (or partial pressures of different gases). The configuration also allows separate fluid flow into or out of the sample so that absorption of fluids can be studied during various loading and deformation conditions. This provides a broader range of characterization measurements that currently exists nowhere else.

It will be apparent to those skilled in the art that the pressure on the sample in the system of the invention can be applied in various ways.

For example, if the volume change device is elevated then the difference in head between the triaxial cell and the volume change device supplies the requisite pressure. In this case the port on top of the volume change device is left open and thus, only the atmospheric pressure is applied to the sample. This is shown in FIG. 1.

If the volume change device is pressurized (in this case there is no need to elevate the volume change device) for example, from 0–50 psi or higher, by any regulated pressure source e.g. air supply, the pressure that is applied to the upper port in FIG. 2 of the volume change device will be transmitted by the fluid in the pressure lines or tubes to the specimen.

The crux of the invention resides in the unique configuration of the system, i.e., the unique arrangement of the parts with respect to each other. For example, the cup is not restricted in its motion by any hose or pipe so that one can measure the volume change by measuring the change in weight of the fluid that is accumulated or released from the cup. In other words, the cup and a scale are arranged in such a way that there are no moving parts. Indeed, any scale or weight measuring device can be substituted for the miniature beam shown in FIG. 3.

A second critical feature of the invention is that it is operable at very low pressures, i.e., when the pressure is simply applied by raising the volume change device and leaving the upper port thereon open to the air. Those skilled in the art will be aware, however, that the invention is also operable under moderate or high pressures, i.e., if the volume change device is pressurized, provided that pressure-resistant components are employed where necessary in constructing the system.

The precise nature of the volume change sensor is not overly critical to the invention. Preferably, the volume change sensor comprises a simple weight scale or strain gage system as shown in FIG. 3; however, those skilled in the art that any such device, preferably having little or no moving parts, may be employed in the practice of the invention.

The confining fluid is preferably water; however, it will be understood by those skilled in the art that any suitable fluid may be employed. For example, under extremely high pressures, an oil, such as castor oil, may be employed.

EXAMPLES

Two series of tests were carried out, one on alumina (mean particle size 100 μm) and the other on microcrystalline cellulose (mean particle size 20 μm) using the enhanced triaxial equipment of the present invention.

The objective was to test whether the new system could capture with improved accuracy the influence of the initial porosity on the response under confined conditions. The first series of tests was done using the setup in FIG. 1. A set of tests was performed for different initial densities at two low confining pressures of 9.7 KPa (1.4 psi) and 16 KPa (2.32 psi) respectively. The results are shown in FIGS. 4,5,6 and 7.

The second series of tests was carried out to obtain the elastic moduli of microcrystalline cellulose at two confining pressures of 68.95 KPa (10 psi) and 344.74 KPa (50 psi). These results are shown in FIGS. 8, 9, 10, 11, 12, 13, 14 and 15.

The system of the present invention enables the extension of the range and accuracy of the quasistatic material characterization measurements, especially the volumetric strain data. This enhancement in measurements is one step forward in the development of enhanced 3-dimensional constitutive models. The enhanced data allows one to focus on constitutive model enhancements that would be necessary to handle a wider range of loading and deformation conditions.

All industries at some time or another are forced to deal with powder or other particulate system handling and processing. The reliability of the processes involved and the transportation and handling of these powders depends upon their flowability as related to preliminary compaction. In order to make any predictions as to flowability, it is necessary to measure the flow properties of the powders. Flowability is also important in comparing similar or new bulk solids to determine whether the products cab fulfill the requirements of quality control. All of the above can be achieved with the triaxial system of the invention. The system can also be used to calibrate existing testers for measuring flow properties of particulate solids.

Any particulate solid may be tested according to the method and system of the invention; e.g., silica, alumina, microcrystalline cellulose, polymers such as polyethylene, and the like.

We claim:

1. A triaxial system for testing particulate matter under substantially dry triaxial load conditions comprising:
   a housing means fillable with confining fluid for providing confining pressure on a sample of dry particulate matter to be tested, the sample having a top and a bottom, the housing having an opening therein through which a portion of a load piston sealingly extends for providing a load on the sample,
   sample mounting means for mounting the sample within the housing, the sample mounting means including a top end platen for mounting at the top and a bottom end platen for disposition at the bottom of the sample,
   at least one flexible, impermeable membrane for enclosing the surface of the sample other than its ends and preventing the confining fluid from directly contacting the sample and preventing sample from being expelled from the portion of the sample covered by the membrane,
   fluid passage means connecting said housing to a volume change sensor for freely delivering confining fluid thereto, wherein
   said volume change sensor is adapted to measure the volume of confining fluid delivered thereto through said fluid passage means, and wherein said volume change sensor comprises means for measuring the weight of the confining fluid delivered thereto.

2. The triaxial test system of claim 1 wherein the confining fluid is water.

3. The triaxial test system of claim 1 wherein the top end platen and the bottom end platen each has a substantially flat planar surface for contacting the sample.

4. The triaxial test cell system of claim 1 wherein the membrane extends partially over each end platen and is secured thereto.

5. The triaxial test system of claim 1 wherein the sample to be tested is alumina, microcrystalline cellulose.

6. The triaxial system of claim 1 additionally comprising wiring connected to the volume change sensor, the wiring connectible to a system for monitoring and recording changes sensed by the volume change sensor.

7. A test method for triaxially testing a sample comprising dry particulate material under dry triaxial load conditions comprising providing:
   a housing means fillable with confining fluid for providing confining pressure on said sample of dry particulate matter to be tested, the sample having a top and a bottom, the housing having an opening therethrough through which a portion of a load piston sealingly extends for providing a load on the sample,
   sample mounting means for mounting the sample within the housing, the sample mounting means including a top end platen for mounting at the top and a bottom end platen for disposition at the bottom of the sample,
   at least one flexible impermeable membrane for enclosing the surface of the sample other than its ends and preventing the confining fluid from directly contacting the sample and preventing sample from being expelled from the portion of the sample covered by the membrane,
   fluid passage means connecting said housing to a volume change sensor for freely passing confining fluid therethrough,
   the test method comprising:
   placing the sample in said sample mounting means,
   loading the sample by introducing a confining fluid under pressure into said housing to provide a constant confining pressure on the sample,
   allowing the sample's pore pressure to equilibrate with the pressure of the confining fluid,
   applying a load piston to the top end platen to apply a known load on the sample, the piston sealingly extending through the confinement vessel to contact the sample, and
   measuring and recording the volume of confining fluid displaced through said fluid passage means connecting said housing to said volume change sensor during said test.

8. The method of claim 7 wherein the pressure applied is substantially atmospheric pressure.

* * * * *